(12) United States Patent
Haynes et al.

(10) Patent No.: US 6,770,282 B1
(45) Date of Patent: Aug. 3, 2004

(54) CATIONIC LIPID-MEDIATED ENHANCEMENT OF NUCLEIC ACID IMMUNIZATION OF CATS

(75) Inventors: Joel R. Haynes, Mazomanie, WI (US); Ramani S. Wonderling, Waukegan, IL (US); Dan T. Stinchcomb, Fort Collins, CO (US)

(73) Assignee: Heska Corporation, Fort Collins, CO (US)

( * ) Notice: Subject to any disclaimer, the term of this patent is extended or adjusted under 35 U.S.C. 154(b) by 0 days.

(21) Appl. No.: 09/830,221

(22) PCT Filed: Oct. 22, 1999

(86) PCT No.: PCT/US99/24769

§ 371 (c)(1),
(2), (4) Date: Aug. 10, 2001

(87) PCT Pub. No.: WO00/24428

PCT Pub. Date: May 4, 2000

Related U.S. Application Data

(60) Provisional application No. 60/122,446, filed on Mar. 2, 1999, now abandoned, and provisional application No. 60/105,469, filed on Oct. 23, 1998, now abandoned.

(51) Int. Cl.[7] ..................... A61K 39/39; A61K 39/385; A61K 39/12; A61K 39/205
(52) U.S. Cl. ............................. 424/196.11; 424/193.1; 424/204.1; 424/224.1
(58) Field of Search ................................ 424/450, 461, 424/193.1, 196.11, 197.11, 204.1, 207.1, 216.1, 221.1, 224.1, 229.1, 234.1, 265.1, 269.1, 275.1

(56) References Cited

U.S. PATENT DOCUMENTS

| | | | |
|---|---|---|---|
| 4,726,946 A | | 2/1988 | Bass et al. ..................... 424/89 |
| 5,505,941 A | * | 4/1996 | Paoletti ....................... 424/93.2 |
| 5,703,055 A | | 12/1997 | Felgner et al. ................ 514/44 |

FOREIGN PATENT DOCUMENTS

| WO | WO 95/30019 | | 11/1995 |
|---|---|---|---|
| WO | WO 98/03660 | * | 1/1998 |
| WO | WO 99/66879 | | 12/1999 |

OTHER PUBLICATIONS

Cuisinier et al. Vaccine. Jul., 1997; 15 (10): 1085–1094.*
Yokoyama et al. FEMS. 1996; 14: 221–230.*
Ray et al. Vaccine. 1997; 15 (8): 892–895.*
McCluskie et al. Antisense and Nucleic Acid Drug Development. 1998; 8: 401–414.*
Davis et al., 1997, *Vaccine*, vol. 15, No. 8, pp. 849–852.
Donnelly et al., 1997, *Annu. Rev. Immunol.*, vol. 15, pp. 617–648.
Fynan et al., 1993, *Proc. Matl. Acad. Sci. USA*, vol. 90, pp. 11478–11482.
Gramzinski et al., 1998, *Molecular Medicine*, vol. 4, pp. 109–118.
Gregoriadis et al., 1997, *FEBS Letters*, vol. 402, pp. 107–110.
Ishii et al., 1997, *Aids Research and Human Retroviruses*, vol. 13, No. 16, pp. 1421–1428.
McCluskie et al., 1998, *Antisense & Nucleic Acid Drug Development*, vol. 8, pp. 401–414.
Norman et al., 1997, *Vaccine*, vol. 15, No. 8, pp. 801–803.
Osorio et al., 1999, *Vaccine*, vol. 17, pp. 1109–1116.
Philip et al., 1994, *Molecular and Cellular Biology*, pp. 2411–2418.
Stamatatos et al., 1988, *Biochemistry*, vol. 27, pp. 3917–3925.
Stopeck et al., 1998, *Cancer Gene Therapy*, vol. 5, No. 2, pp. 119–126.
Xiang et al., 1996, *Virology*, vol. 219, pp. 220–227.
Yokoyama et al., 1996, *FEMS Immunology and Medical Microbiology*, vol. 14, pp. 221–230.

* cited by examiner

*Primary Examiner*—James Housel
*Assistant Examiner*—Shanon Foley
(74) *Attorney, Agent, or Firm*—Heska Corporation

(57) ABSTRACT

The present invention relates to a method to introduce a nucleic acid molecule into a felid by administration of a nucleic acid-cationic lipid complex composition. The method includes the step of administering to the felid, by a parenteral route, a nucleic acid-cationic lipid complex to elicit and/or enhance an immune response. In one embodiment, this method enhances the immune response in a felid compared to a method in which a naked DNA vaccine is administered to a felid. Also provided is a method to deliver a nucleic acid to a felid. This method comprises parenterally administering to the felid a composition that includes a nucleic acid molecule complexed with a cationic lipid.

16 Claims, No Drawings

CATIONIC LIPID-MEDIATED ENHANCEMENT OF NUCLEIC ACID IMMUNIZATION OF CATS

This application is a U.S. national stage application of PCT International Application No. PCT/US99/24769 filed Oct. 22, 1999 and claims priority to provisional application 60/122,446, filed Mar. 2, 1999, now abandoned, and provisional application 60/105,469 filed Oct. 23, 1998, now abandoned.

FIELD OF THE INVENTION

The present invention relates to a method to introduce a nucleic acid molecule into a felid by administration of a nucleic acid molecule-cationic lipid complex composition. In particular, the present invention relates to the parenteral administration of a nucleic acid molecule-cationic lipid complex to elicit and/or enhance an immune response to the protein encoded by the administered nucleic acid molecule.

BACKGROUND OF THE INVENTION

Introduction of DNA into an animal for the purpose of eliciting an immune response is often referred to as DNA vaccination. DNA vaccination represents a means of expressing an antigen in vivo for the generation of humoral and cellular immune responses. DNA vaccines employ genes encoding antigens, rather than using the proteins themselves, to induce immune responses. The DNA, upon administration to the host, is transcribed and translated in vivo to produce an antigen. Processing and presentation of the antigen stimulates the animal's immune system to elicit a humoral and/or cellular response to the antigen. This immune response can potentially confer protective immunity to the animal.

DNA vaccines appear to have advantages over protein antigen-based vaccines, standard "killed" pathogen vaccines, live, attenuated vaccines, and recombinant viral vector vaccines. For example, DNA vaccines appear to be more effective in producing an antigen with a properly folded, native three-dimensional conformation and in generating a cellular immune response than arc protein antigens. DNA vaccines also do not exhibit at least some of the safety problems of killed, live or virally-vectored vaccines. For example, a killed virus preparation may contain residual live viruses or may need to be mixed with reactogenic adjuvants, such as those associated with vaccine-related fibrosarcomas in cats, in order to stimulate an effective immune response. An attenuated virus may mutate and revert to a pathogenic phenotype. Viral vector vaccines genetically engineered to express a gene encoding the desired antigen may stimulate the production of antibodies that react with the virus as well; such antibodies may render futile any further attempt to use that virus as a vector, even with a different gene insert. In contrast, DNA vaccines apparently are non-reactogenic and; if they elicit an immune response, that response is targeted against the antigen of choice.

DNA vaccines typically include a bacterial plasmid, a strong viral promoter, the gene of interest, and a polyadenylation/transcriptional termination sequence. The plasmid is typically grown in bacteria, purified, dissolved in a saline solution, and then simply injected into an animal. Current understanding of how to use DNA vaccines to generate an effective immune response, however, is not complete. Most of our understanding of the mechanisms of DNA vaccine action is derived from rodent studies. In mice, bone marrow-derived antigen-presenting cells have been shown to induce cytotoxic T lymphocyte responses following intramuscular inoculation of naked plasmid DNA. In some cases, DNA vaccination has also been shown to stimulate antigen-specific antibodies, some of which may be neutralizing antibodies. DNA vaccines have also been administered to large animals, albeit with varying degrees of success. While there are some clear examples of DNA vaccine efficacy in large animals, other studies cite relatively weak responses, requirement for large amounts of DNA, or the need for multiple immunizations. As such, it is apparent that further technology development is required to maximize DNA vaccine efficacy in humans and large animals.

Immune responses to DNA vaccination appear to vary according to the vehicle used with the DNA vaccine, the antigen expressed by the DNA vaccine, the route of administration, and the species of mammal into which the DNA vaccine is injected. Investigators have used different vehicles and/or genes encoding cytokines and other stimulatory molecules in an attempt to enhance the immune response to the antigens encoded by DNA vaccines with mixed success. Although cationic lipids have been used to deliver nucleic acids to cells in vitro and in vivo, there is no consensus in the literature about whether cationic lipids reproducibly enhance the immunogenicity of DNA vaccines. Gregoriadis et al., 1997, FEBS Letters 402, 107, reported that intramuscular (I.M.) injection of DNA encoding HBsA "entrapped" in cationic liposomes into mice elicited an enhanced immune response compared to I.M. injection of "naked" DNA encoding HBsA, whereas DNA encoding HBsA merely "complexed" with cationic lipid generated a reduced immune response compared to "naked" DNA. Ishii et al., 1997, AIDS Research and Human Retroviruses 13, 1421–1424, demonstrated enhanced immune responses to V3 peptide following I.M., intraperitoneal (I.P.) intradermal (I.D.) intranasal (I.N.) or subcutaneous (S.Q.) administration to mice.

Other investigators, in contrast, found no enhancement of immune responses when cationic lipids were used as a vehicle for DNA vaccines in mice. For example, Davis, et al., 1997, Vaccine 15, 849, found that DNA vaccines encoding the Hepatitis B surface antigen formulated with varying amounts of cationic lipids performed no better than DNA alone in inducing a humoral response in mice. Gramzinski, et al., 1998, Molecular Medicine 4, 109, reported that Aotus monkeys administered DNA vaccines encoding HBsA either with or without cationic lipids (CELLFECTIN®, 10:1 DNA:lipid) by I.M. injection did not seroconvert. Clearly, there is no consensus regarding whether cationic lipids reproducibly act to elicit or enhance immune responses to DNA vaccines.

There also appears to be a high degree of variability of the efficacy of DNA vaccines between different routes of administration. Ishii et al, ibid., for example, found in mice that I.M. and I.N. administration of DNA vaccines generated approximately equivalent immune responses, but that I.P. administration was less effective, and that I.D. and S.Q. administration routes were even less effective. Ishii et al, ibid., found these differences to be consistent regardless of whether DNA was used alone or formulated with cationic lipids. Yokoyama et al, 1996, FEMS Immuno Med Microbio 14, 221–230, showed that I.V. administration of a DNA vaccine generated a better immune response than I.M. administration of the same vaccine in mice.

Taken together, these data indicate that there is a high degree of variability in the effectiveness of DNA vaccines and in the ability of cationic lipids to enhance the effectiveness of DNA vaccines both within and between species and routes of administration.

There are a number of diseases in cats which lead to significant morbidity and mortality. It would be desirable to provide novel and safe vaccines that would confer protective immunity to these diseases. That there is still a need for such vaccines is underscored not only by the association of some feline vaccines with the development of fibrosarcomas but also by the finding that I.M. administration of naked DNA encoding either human growth hormone (hGH) or rabies virus glycoprotein G into domestic cats resulted in complete seroconversion, even after two immunizations (Osorio et al, 1999, Vaccine, in press). These results indicate that parenteral naked DNA vaccination efficacy in cats is inferior to results obtained in mice, and that the efficacy achieved using naked DNA in cats is not sufficient to protect cats from disease. Thus, there remains a need to provide a method to elicit and to enhance the immune response to antigen encoded by DNA vaccines in cats.

SUMMARY OF THE INVENTION

The present invention relates to a method to elicit an immune response to an antigen in a felid. This method includes the step of parenterally administering to the felid a composition comprising a nucleic acid molecule encoding the antigen in which the nucleic acid molecule is complexed with a cationic lipid. In one embodiment, this method enhances the immune response in a felid compared to a method in which a naked DNA vaccine is administered to a felid. Also provided is a method to deliver a nucleic acid molecule to a felid. This method comprises parenterally administering to the felid a composition that includes a nucleic acid molecule complexed with a cationic lipid.

DETAILED DESCRIPTION

The present invention relates to a method to elicit an immune response to an antigen in a felid. The method includes the step of parenterally administering to the felid a composition comprising a nucleic acid molecule encoding the antigen in which the nucleic acid molecule is complexed with a cationic lipid. The ability of such a method to elicit an immune response to the antigen encoded by the nucleic acid molecule is new and surprising. Until recently, the general perception of those skilled in the art was that cationic lipids did not enhance the ability of a nucleic acid molecule to elicit an immune response, compared to, for example, delivery of a naked, or unformulated, nucleic acid molecule (i.e., a nucleic acid molecule that is not complexed with, for example, a lipid or other transfection-facilitating agents). Recent studies, cited above, have provided conflicting results: although two studies in mice demonstrated that cationic lipids enhanced the ability of DNA to elicit an immune response, a third study concluded that cationic lipid-complexed DNA was no better than naked DNA at eliciting an immune response. In addition, monkeys administered a nucleic acid molecule-cationic lipid complex did not exhibit seroconversion to the antigen encoded by the nucleic acid molecule. Furthermore, the inventors have demonstrated that while parenteral administration to a felid of a nucleic acid molecule complexed with a cationic lipid results in the felid successfully seroconverting in response to the antigen encoded by the nucleic acid molecule, intranasal administration of such a composition did not result in seroconversion. Thus, the ability to demonstrate seroconversion in cats parenterally administered a nucleic acid molecule complexed with a cationic lipid is completely unpredictable based on previous studies and, as such, is inventive.

One embodiment of the present invention is the use of a composition comprising a nucleic acid molecule encoding an antigen complexed with a cationic lipid to elicit an immune response in a felid. It is to be noted that the term "a" or "an" entity refers to one or more of that entity;, for example, a nucleic acid molecule, an antigen, and a cationic lipid refers to one or more nucleic acid molecules, antigens, and cationic lipids, respectively; or to at least one nucleic acid molecule, antigen, and cationic lipid, respectively. As such, the terms "a" (or "an"), "one or more" and "at least one" can be used interchangeably herein. It is also to be noted that the terms "comprising", "including", and "having" can be used interchangeably. Furthermore, a member of a group that is "selected from the group consisting of" refers to one or more of members of that group, including combinations thereof.

A nucleic acid molecule of the present invention also referred to herein as a nucleic acid, can be DNA or RNA. In one embodiment, a nucleic acid molecule encodes an antigen that elicits an immune response in a felid. As such, a nucleic acid molecule can simply be a molecule that encodes such an antigen, i.e., a coding region, or the nucleic acid molecule can comprise a coding region operatively linked to a regulatory sequence. As used herein, the phrase operatively linked refers to the joining of a coding region to one or more regulatory sequences such that the coding region is expressed using such regulatory sequencers) in a felid. Examples of such regulatory sequences include transcription control sequences and translation control sequences that can be recognized by felid cellular mechanisms in order to effect transcription and translation of a coding region. Transcription control sequences are sequences that control the initiation, elongation, and termination of transcription (e.g., promoters, enhancers, introns, polyA sites, terminators). Transmutation control sequences control the initiation, elongation and termination of translation. Additional regulatory sequences include signal sequences that effect secretion of a protein from a cell and a combination of a signal sequence and a transmembrane sequence (i.e., membrane anchoring domain) that causes a protein to be partially extracellular and partially retained in the membrane and/or cytoplasm. A preferred nucleic acid molecule of the present invention is a plasmid or viral genome that includes a coding region for the desired antigen operatively linked to strong eukaryotic regulatory sequences, including a strong promoter and strong transcription termination/polyadenylation sequences. A preferred plasmid can replicate in bacteria. Procedures by which such a nucleic acid molecule is produced are known to those skilled in the art, and are disclosed, for example, in Sambrook et al., 1989, *Molecular Cloning: A Laboratory Manual*, Cold Spring Harbor Labs Press. Appropriate plasmids are known in the art,and may include, but are not limited to, pUC19 and BLUESCRIPT®. A preferred plasmid is pUC19. Appropriate regulatory sequences are known to those skilled in the art. For example, a suitable promoter includes, but is not limited to the cytomegalovirus immediate early promoter (CMV IE) with or without intron A, a long terminal repeat (LTR) promoter from a retrovirus, or a strong cellular promoter such as β-actin, with CMV IE with intron A being preferred. Similarly, suitable transcription termination sequences include, but are not limited to, bovine growth hormone, SV40 virus or rabbit beta-globin polyadenylation sequences, with a bovine growth hormone sequence being preferred.

A suitable antigen is any antigen that effects an immune response, and as such includes allergens and autoantigens as well as other antigens. An antigen, as used herein, can refer to the full-length antigen or any portion thereof that is capable of eliciting an immune response. Preferred antigens are those that elicit an immune response that protects an animal from disease. Examples of such antigens include, but are not limited to, a protozoan parasite antigen, a helminth parasite antigen, an ectoparasite antigen, a fungal antigen, a bacterial antigen, and a viral antigen. Examples of viral antigens include, but are not limited to, antigens from adenoviruses, caliciviruses, coronaviruses, distemper viruses, hepatitis viruses, herpesviruses, immunodeficiency viruses, infectious peritonitis viruses, leukemia viruses, oncogenic viruses, papilloma viruses, parainfluenza viruses parvoviruses, rabies viruses, and reoviruses, as well as other cancer-causing or cancer-related viruses. Examples of bacterial antigens include, but are not limited to, antigens from Actinomyces, Bacillus, Bacteroides, Bordetella, Bartonella, Borrelia, Brucella, Campylobacter, Capnocytophaga, Clostridium, Corynebacterium, Coxiella, Dermatophilus, Enterococcus, Ehrlichia, Escherichia. Francisella, Fusobacterium, Haemobartonella. Helicohacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia. Examples of fungal antigens include, but are not limited to, antigens from Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Hisioplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha. Example of protozoan and helminth parasite antigens include, but are not limited to, antigens from Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris, Uncinaria, and Wuchereria. Examples of ectoparasite antigens include, but are not limited to, antigens (including protective antigens as well as allergens) from fleas, ticks, including hard ticks and soft ticks; flies, such as midges, mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs. Additional examples of suitable allergens include food, grass, weed, tree pollen, other animal and other plant allergens.

Preferred antigens include, but are not limited to, a calicivirus antigen, a coronavirus antigen, a herpesvirus antigen, an immunodeficiency virus antigen, an infectious peritonitis virus antigen, a leukemia virus antigen, a panleukopenia virus antigen, a parvovirus antigen, a rabies virus antigen, a Bartonella antigen, a Yersinia antigen, a Dirofilaria antigen, a Toxoplasma antigen, a tumor antigen, a flea antigen, a flea allergen, a midge antigen, a midge allergen, a mite antigen, a mite allergen, a ragweed allergen, a ryegrass allergen, a cat allergen, a dog allergen, a Bermuda grass allergen, a Johnson grass allergen, or a Japanese cedar pollen allergen. Particularly preferred antigens include a rabies virus glycoprotein G antigen; heartworm PLA2, P39, P4, P22U, Gp29, astacin, cysteine protease, macrophage migration inhibitory factor, venom allergen, TPX-1, TPX-2, transglutaminase, ankyrin, asparaginase, calreticulin, cuticulin, and aromatic amino aid decarboxylase antigens; flea serine protease, cysteine protease, aminopeptidase, serpin, carboxylesterase, juvenile hormone esterase, chitinase, epoxide hydrolase, ecdysone, ecdysone receptor, and ultraspiracle protein antigens; flea salivary antigens; Yersinia F1 and V antigens; and *Toxoplasma gondii* antigens such as those disclosed in PCT Patent Publication No. WO 99/32633, published Jul. 1, 1999, by Milhausen et al. Additional examples of suitable and preferred allergens are disclosed in U.S. Pat. No. 5,945,294, issued Aug. 31, 1999, by Frank et al. (U.S. Pat. No. 5,945,294); U.S. Pat. No. 5,958,880, issued Sep. 28, 1999, by Frank et al. (U.S. Pat. No. 5,958,880); PCT Patent Publication No. WO 98/45707, published Oct. 15, 1998, by Frank et al. (WO 98/45707); and PCT Patent Publication No. WO 99/38974, published Aug. 5, 1999, by Weber et al. (WO 99/38974).

One embodiment of the present invention is a composition comprising a nucleic acid molecule-cationic lipid complex that further comprises a heterologous nucleic acid molecule encoding an immunomodulator. Such an immunomodulator-encoding nucleic acid molecule can be contained within the same nucleic acid molecule encoding the antigen of the present invention, or can exist as a separate nucleic acid molecule, which can be on the same or separate plasmid or viral genome. The present invention also includes Suitable immunomodulators include compounds that enhance certain immune responses as well as compounds that suppress certain immune responses. Compounds that enhance the immune response include compounds that preferentially enhance humoral immunity as well as compounds that preferentially enhance cell-mediated immunity. Suitable compounds can be selected depending on the desired outcome.

Suitable immunomodulators include, but are not limited to, cytokines, chemokines, superantigens, co-stimulatory molecules, adhesion molecules, and other immunomodulators as well as compounds that induce the production of such immunomodulators. Examples of such compounds include, but are not limited to, granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin 3 (IL-3), interleukin 4 (IL4), interleukin 5 (EL-5), interleukin 6 (IL-6), interleukin 7 (IL7), interleukin 8 (IL-8), interleukin 10 (IL-I0), interleukin 12 (IL-12), interleukin 13 (IL-13), interleukin 18 (IL- 18), interferon gamma, interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), Leishmania elongation initiating factor (LEIF), B7-1, B7-2, CD40, CD40 ligand, ICAM-1, and VCAM.

A composition of the present invention includes a cationic lipid complexed with a nucleic acid molecule encoding an antigen in order to elicit or enhance an immune response to the antigen. As used herein, a cationic lipid is a lipid which has a cationic, or positive, charge at physiologic pH. Cationic lipids can have a variety of forms, including liposomes or micelles. Whether a cationic lipid occurs primarily as a liposome or a micelle can be manipulated by methods known in the art; for example, a freezing and thawing of cationic lipids in aqueous solution will encourage formation of liposomes, rather than micelles. A nucleic acid molecule complexed with a cationic lipid may also be referred to as a nucleic acid molecule-cationic lipid complex, a lipoplex or a complex of the present invention. A complex of the present invention that elicits an immune response is a complex of a nucleic acid molecule which encodes an antigen with a cationic lipid. As used herein, the term complexed with, which is equivalent to complexed to, refers to any method by which a nucleic acid molecule interacts (e.g. binds, comes into contact with a cationic lipid.) Such an interaction can include, but is not limited to encapsulation of a nucleic acid molecule into a cationic liposome, association of a nucleic acid molecule and cationic lipid characterized by non-covalent, ionic charge interactions, and other types of associations between nucleic acid molecules and cationic lipids known by those skilled in the art. It is preferred that cationic lipids have a cationic group, such as a quaternary amine group, and one or more lipophilic groups, such as saturated or unsaturated alkyl groups having from about 6 to 30 carbon atoms. Cationic lipid compositions suitable for use in the present invention include lipid compositions comprised of one type of lipid, or lipid compositions comprised of more than one type of lipid. If there is more than one type of lipid present in a lipid composition, it is necessary that the overall net charge of the lipid composition is cationic, i.e. positive; however, as long as the overall net charge of the lipid composition is cationic, individual lipid types may be neutral or even anionic in charge. A composition of the present invention includes a cationic lipid that is suitable in accordance with the present invention. Cationic lipids suitable for use in the present invention include commercially available cationic lipids, for example DOTMA, available under the trademark name of LIPOFECTIN®, available from Life Technologies Inc., (LTI), Gaithersburg, Md. and DDAB, available from Boehringer-Mannheim, Indianapolis, Ind. In addition, suitable cationic lipids can be synthesized as described in the literature; see, for example, Felgner et al., 1987, PNAS 84 7413-7417 regarding the preparation of DOTAP; Douar et al, 1996, Gene Ther 3(9), 789-796 regarding the preparation of Lipid 67; Wheeler et al., 1996, Biochim Biophys Acta 1280(1), 1–11 regarding the preparation of DMRIE; McLean et al., 1997 Am J Physiol 273, H387–404 regarding the preparation of DOTIM; and Hofland et al., 1997, Pharm Res 14(6), 742–749 regarding the preparation of DOSPA. Other suitable cationic lipid compounds are described in the literature. See, for example, Stamatatos et al., 1988, Biochemistry 27, 3917–3925 and Eibl, et al., 1979, Biophysical Chemistry 10, 261–271. Preferred cationic lipids include the class of lipids known as tetramethyltetraalkyl spermine analogs, described by McCluskey et al., (1998), *Antisense and Nucleic Acid Drug Development*, vol. 8, pp 40–14. Lipids of this type include tetramethyltetralaurylspermine, tetramethyltetramyristylspermine, tetramethyltetrapalmitoylspermine, and tetramethyltetraoleoylspermine. The following lipids, obtained from LTI are of the tetramethyltetraalkyl spermine class, with the alkyl groups containing fatty acid chains of length longer than oleic acid. These lipids art denoted as LTI lipids 4251-781-1, 4251-106-3, 4518-52, D304-200, 4521-52-3, 4251-106-4, 4251-781-2, 4518-53, 4518-31, 4519-30, 4519-34, and 2518-111. Preferred cationic lipids include LTI lipid 4251-781-1, LTI lipid 4251-106-3, and LTI lipid 4518-52. In one embodiment, tetramethyltetraalkyl spermine lipids are formulated with a neutral lipid, such as dioleylphosphatidylethanolamine (DOPE).

A nucleic acid molecule-cationic lipid complex can be formed by using techniques known to those skilled in the art, examples of which are described in the Examples section. A complex can be formed, for example, by adding a cationic lipid solution to a nucleic acid molecule, preferably an endotoxin-free nucleic acid molecule, at concentrations appropriate for the present invention, and mixing, for example by pipetting. Preferable nucleic acid molecule-to-cationic lipid ratios are from about 10:1 weight nucleic acid molecule: weight cationic lipid, (e.g. microgram ($\mu$g) nucleic acid molecule to $\mu$g cationic lipid) to about 1:10 weight nucleic acid molecule: weight cationic lipid. More preferable are ratios from about 1:2 weight of nucleic acid molecule: cationic lipid to about 4:1 weight of nucleic acid molecule: cationic lipid. In a preferred embodiment, the nucleic acid molecule-cationic lipid complex is incubated at room temperature for about 30 minutes before administration. A nucleic acid molecule-cationic lipid complex can be dehydrated and rehydrated using techniques known to those skilled in the art; for example, the complex can be frozen in liquid nitrogen and lyophilized at 150 milliTorr, then reconstituted in solution for injection.

A dose of a nucleic acid molecule-cationic lipid complex to administer to a cat can be reported as the amount of nucleic acid molecule administered to a cat. A preferred dose of a nucleic acid molecule-cationic lipid complex to administer to a cat includes from at least one nanogram (ng) of nucleic acid to about 10 milligram (mg) of nuleic acid molecule. More preferred is a dose range that includes from about 1 $\mu$g nucleic acid molecule to about 1 mg of nucleic acid molecule. Particularly preferred is a dose ranging from about 75 $\mu$g of a nucleic acid molecule to about 300 $\mu$g of a nucleic acid molecule.

A nucleic acid molecule-cationic lipid complex composition of the present invention can be formulated in an excipient that the animal to be treated can tolerate. As such, the present invention includes administration of a composition comprising a nucleic acid molecule-cationic lipid complex, wherein the composition further comprises an excipient. Examples of such excipients include water, saline, Ringer's solution, dextrose solution, Hank's solution, and other aqueous physiologically balanced salt solutions. Other useful formulations include suspensions containing viscosity enhancing agents, such as sodium carboxymethylcellulose, sorbitol, mannitol, or dextran. Excipients can also contain minor amounts of additives, such as substances that enhance isotonicity and chemical stability. Examples of buffers include phosphate buffer, bicarbonate buffer and Tris buffer. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the nucleic acid molecule-cationic lipid complex can also include an adjuvant and/or a carrier. One advantage of a nucleic acid moleculecationic lipid complex is that adjuvants and carriers are not required to produce a composition that administration thereof will elicit an immune response. However, it should be noted that use of adjuvants or carriers is not precluded by the present invention. Adjuvants are typically substances that generally enhance the immune response of an animal to a specific antigen. Suitable adjuvants include, but are not limited to, other bacterial cell wall components; aluminum-based salts; calcium-based salts; silica; polyriucleotides; toxins, such as cholera toxin; toxoids, such as cholera toxoid; serum proteins; other viral coat proteins; other bacterial-derived preparations; block copolymer adjuvants, such as Hunter's Titermax™ adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

An immune response to an antigen includes a humoral, i.e. antibody, response to that antigen and/or a cell-mediated response to that antigen. Methods to measure an immune response are known to those skilled in the art; examples of such methods are disclosed herein. If one or both types of immune response are present, they may protect the felid from disease caused, for example, by the agent from which the antigen was derived. In accordance with the present invention, the ability of an antigen derived from a disease-causing agent to protect an animal from a disease caused by that disease-causing agent or a cross-reactive agent refers to the ability of a nucleic acid molecule-cationic lipid complex of the present invention to treat, ameliorate and/or prevent disease caused by the disease-causing agent or cross-reactive agent, preferably by eliciting an immune response against the antigen derived from the disease-causing agent. It is to be noted that an animal may be protected by a composition of the present invention even without the detection of a humoral or cell-mediated response to the antigen. Protection can be measured by methods known to those skilled in the art, such as by challenging an animal with the agent against which the animal has mounted a putative immune response. In certain cases, the antibody titer of an animal can be used to demonstrate protection. For example, it is known that animals that elicit an antibody response against a rabies glycoprotein G antigen are protected if their sera exhibits a rapid focus fluorescent inhibition test (RFFIT) titer of rabies virus neutralizing antibodies of greater than 1:5. As used herein, an animal that elicits an immune response to an antigen is an animal that has been immunized with that antigen.

The biological mechanism for eliciting and/or enhancing an immune response by the use of a nucleic acid molecule-cationic lipid complex composition of the present invention has not been elucidated, but, without being bound by theory, the inventors believe that the mechanism is likely related to the ability of these compositions to protect DNA from nuclease attack, to facilitate the transfection of both muscle cells and professional antigen presenting cells (APC) in vivo, to increase levels of expression in transfected cells, and/or to distribute DNA to lymphoid organs.

A felid, as used herein, is a member of the family Felidae. Examples of felids include domestic cats, wild cats, and zoo cats. Examples of cats, include, but are not limited to, domestic cats, lions, tigers, leopards, panthers, cougars, bobcats, lynx, jaguars, cheetahs, and servals. A preferred cat to immunize is a domestic cat. The term cat(s) and felid(s) are used interchangeably herein.

As used herein, parenteral administration means administration not through the alimentary canal (e.g. oral administration), but rather by injection through some other route, including but not limited to routes such as subcutaneous, intramuscular (I.M.), intravenous (I.V.), intraperitoneal (I.P.), intradermal (I.D.), intraorbital, intracapsular, intraspinal, and intrasternal. Parenteral administration includes, but is not limited to, administration by any route that includes use of a needle to insert material into the body. Parenteral administration also includes uses of devices other than a syringe and needle to insert material through the skin and or mucosal surfaces into the body, including but not limited to the BIOJECTOR®, POWDERJECT, and MEDIJECT® needleless injection systems. A preferred route of administration includes intramuscular administration using a needle and syringe.

Acceptable protocols to administer therapeutic compositions in an effective manner include individual dose size, number of doses, and frequency of dose administration. Typically, the first administration of a composition intended to elicit an immune response is called the primary (or prime) administration, also known as the pre-boost. Additional administrations intended to "boost" or increase an immune response to an antigen are termed booster administrations. Determination of a protocol to elicit an immune response in a cat using a nucleic acid molecule-cationic lipid complex of the present invention can be accomplished by those skilled in the art. In one embodiment of the present invention, a nucleic acid molecule encoding a desired antigen complexed with cationic lipid need only be administered once by a route appropriate to the present invention (e.g. parenteral) to stimulate an immune response against the antigen. In a preferred embodiment, such an administration protects the felid from the agent from which the antigen was derived or from an agent against which the immune response is cross-protective.

In one embodiment, administration of a complex of the present invention to a felid in order to elicit an immune response actually enhances the immune response generated by the felid as compared to the immune response generated upon administration of a naked DNA vaccine to a felid, wherein the naked DNA vaccine consists essentially of a naked DNA molecule; i.e., a DNA molecule that is not complexed with lipids. Finding that a complex of the present invention enhances an immune response is surprising both in view of the conflicting studies known to those skilled in the art as described herein as well as in view of the studies described in more detail in the Examples, in which administration of naked DNA vaccines to cats elicited immune responses in only some cats within each group, or population, tested, whereas administration of a complex of the present invention could result in up to 100% seroconversion of all cats in a population tested. As used herein, enhancement of the immune response can include increasing the amount, or titer, of antibody elicited by a complex of the present invention that encodes an antigen to the desired antigen and/or agent from which the antigen was derived as compared to the titer of antibody generated by a naked DNA vaccine that encodes the same antigen. In one embodiment, such an enhancement can be induction of no antibody titer with a naked DNA vaccine to induction of a protective antibody titer with a complex of the present invention. Enhancement of an immune response can also refer to augmentation of the cell-mediated response to the antigen and/or agent encoded by a complex of the present invention as compared to the response generated by a naked DNA vaccine encoding the same antigen. Enhancement of immune response can also include conferring or augmenting protection from disease by a complex of the present invention compared to the protection, if any, conferred by a naked DNA vaccine encoding the same antigen. In one embodiment, enhancement of the immune response includes increasing the likelihood of a cat seroconverting in response to antigen encoded by a complex of the present invention in comparison to the likelihood of the cat responding to the same antigen encoded by a naked DNA vaccine. In other words, in a group of cats being vaccinated with a complex of the present invention, a greater number of cats will seroconvert in response to antigen encoded by the complex rather than to the same antigen encoded by a naked DNA vaccine. Preferably, the likelihood that a cat will seroconvert when administered a single dose of a complex of the present invention that encodes an antigen is at least about 50%, preferably at least about 75%, more preferably at least about 90% and even more preferably at least about 100%. In the case where a primary and booster administration of the complex is administered, the likelihood that a cat will seroconvert is preferably at least about 75%, more preferably at least about 90%, and even more preferably at least about 100%.

The present invention includes a method to administer a nucleic acid molecule to a felid. The method includes the step of parenterally administering a composition comprising said nucleic acid molecule complexed with a cationic lipid. Such a nucleic acid molecule can encode either a protein or a RNA molecule. In one embodiment, the nucleic acid molecule encodes a protein or RNA molecule that, when expressed at an appropriate level, has a protective effect upon the cat. As used herein, a protein refers to a full-length protein or any portion thereof that is at least about 5 amino acids in length and has a useful function, including, but not limited to, ability to elicit an immune response, elicit an immunomodulatory effect (e.g., an immunomodulator that stimulates or reduces the immune response), effect gene therapy, effect enzyme activity, or otherwise effect cell division, differentiation, development and cell death. As used herein, a RNA molecule refers to any RNA species that can be encoded by a nucleic acid molecule, including, but not limited to antisense RNA, a molecule capable of triple helix formation, a ribozyme, or other nucleic acid-based drug compound. As such, any protein or RNA molecule that can be expressed at an appropriate level in a cat, which protects a cat from disease, would be included in this invention. Diseases from which to protect a felid include, but are not limited to, infectious diseases, genetic diseases, oncological diseases, and other metabolic diseases, including diseases that lead to abnormal cell growth, degenerative processes, and immunological defects. Compositions of the present invention can protect animals from a variety of diseases including, but not limited to, allergies, arthritic diseases, autoimmune diseases, cancers, cardiovascular diseases, graft rejection, hematopoietic disorders, immunodeficiency diseases, immunoproliferative diseases, immunosuppressive disorders, infectious diseases, inflammatory diseases, jaundice, septic shock, and other immunological defects, as well as other genetic or metabolic defects. Methods to produce and use a composition comprising any nucleic acid molecule of the present invention complexed with any cationic lipid of the present invention are as described herein.

The following examples are provided for the purposes of illustration and are not intended to limit the scope of the present invention.

EXAMPLES

Example 1

This Example demonstrates the production of a nucleic acid molecule of the present invention.

A nucleic acid molecule encoding human growth hormone (hGH) was constructed using plasmid pHGH 107 (available from American Type Culture Collection, Manassis, Va.), which encodes hGH amino-acids 1–191, as a polymerase chain reaction (PCR) template. The hGH open reading frame was amplified by PCR using Pfu DNA polymerase (available from Stratagene, La Jolla, Calif.) and the following forward and reverse primers: 5' TTCCCAAC-TATACCACTATCTCGTCTA 3' (SEQ ID NO:1) and 5' CTAGAAGCCACAGCTGCCCTCCACAGAG 3' (SEQ ID NO:2). The PCR product containing the sequence encoding the mature hGH product was ligated into the Nael site of a plasmid containing the human cytomegalovirus immediate early promoter, a translation control sequence, a sequence encoding the signal peptide coding sequence from human tissue plasminogen activator, and a bovine growth hormone poly A sequence. The expression of hGH from this plasmid was confumed following transfection of cells in vitro and was detected using a chemiluminescence assay kit (available from Nichols Institute Diagnostics, San Juan Capistrano, Calif.).

A nucleic acid molecule encoding the rabies virus glycoprotein G was described previously and contains the CMV intron A promoter, the rabies glycoprotein G coding sequence, and the bovine growth hormone polyadenylation sequence. See Osorio, et al. (1999) Vaccine, in press.

Example 2

This Example describes the production of a nucleic acid molecule-cationic lipid complex of the present invention.

Edotoxin free nucleic acid molecules encoding hGH or rabies glycoprotein G were prepared using a commercial kit (Qiagen, Inc., Valencia, Calif.) and the resulting nucleic acid molecules were dissolved in endotoxin-free 10 mM Tris-HCI, pH 7.5, 1 mM EDTA at 2 mg per milliliter (ml) to form a hGH nucleic acid molecule solution and a rabies gG nucleic acid molecule solution, respectively. Cationic lipids 4251-106-3 (also known as 106-3), 4251-781-1 (also known as 781-1), and 4518-52 were obtained from Life Technologies, Inc. (LTI), Gaithersburg, Md. A nucleic acid molecule-cationic lipid complex was formed by adding 250 $\mu$l of the respective cationic lipid solution to 250 $\mu$l of the respective nucleic acid molecule solution, followed by immediate mixing by pipetting. The concentrations of the cationic lipid solutions and of the nucleic acid molecule solutions used were adjusted to give the desired amounts and ratios of nucleic acid molecules to cationic lipids described elsewhere in the Examples. The mixture was incubated at room temperature for 30 minutes before administration. For dehydration and rehydration of a nucleic acid moleculc-cationic lipid complex, the complex was frozen in liquid nitrogen and lyophilized at 150 mTorr, then reconstituted in the original volume of sterile water for injection.

Example 3

This Example describes a method for administering a nucleic acid molecule- cationic lipid complex of the present invention to a felid.

Primary and booster administrations of nucleic acid molecule-cationic lipid complexes prepared as described in Example 2 were injected intramuscularly into the semitendinosus or semimembranosus muscle of domestic cats. Each dose was divided into two equal portions and administered bilaterally into each leg. Sera samples were collected every 10 days for antibody determination.

Example 4

This Example describes methods to measure immune responses generated in response to the administration of nucleic acid molecule-cationic lipid complexes of the present invention.

Antibody responses specific for hGH were determined by ELISA. Briefly, ELISA plate wells were coated with 0.4 micrograms (µg) hGH protein per well (hGH protein available from Genzyme Diagnostics, San Carlos, Calif.) and incubated overnight at 4° C. Unbound antigen was aspirated and the plate was blocked with 2% skimmed milk for 1 hour at 37° C. ELISA plates were washed 3 times with TBS-Tween (150 milliMolar (mM) NaCl, 50 mM Tris-HCl (pH 8.0), 0.1% TWEEN-20) and serially diluted sera samples from vaccinated cats were added and incubated at 37° C for 1 hour. Plates were washed 3 times with TBS-Tween. A biotin conjugated monoclonal anti-cat IgG (1:30,000) (available from Sigma-Aldrich St. Louis, Mo.), was added and incubated for 1 hour at 37° C., followed by the addition of EXTRAVIDIN®-horseradish peroxidase diluted 1:1000, available from Sigma-Aldrich, St. Louis, Mo. After a final incubation at 37° C., for 1 hour, the plates were washed and an o-phenylenediamine dihydrochloride substrate solution, available from Sigma-Aldrich, was added and the plates incubated at room temperature for 30 minutes for color development. The plates were read at 450 nm.

Rabies virus-specific neutralizing antibody response were determined using the Rapid Fluorescent Focus Inhibition test (RFFIT) at the Department of Veterinary Diagnostics, Kansas State University.

T cell proliferation assays were carried out in the following manner. Heparinized blood samples were collected from cats a week after administration of a booster injection as described in Example 5. The lymphocytes were isolated from the blood samples using a percoll gradient (Sigma Chemicals, St Louis, Mo.). The isolated lymphocytes were resuspended in RPMI 1640 (Sigma Chemical) containing 5% normal cat serum, 2 mM L-glutamine (Life Technologies, Bethesda, Md.), 1 mM sodium pyruvate (Life Technologies), 50 µM 2-mercaptoethanol (Life Technologies), 5 µg/mL gentamycin (Sigma Chemical), 0.1 mM MEM non-essential amino acids (Life Technologies), and 1% essential amino acids (Life Technologies) plated at a density of $2 \times 10^3$ cells/well and treated with various concentrations of recombinant human growth hormone (hGH) (Genzyme Diagnostics, Boston, Mass.) for a total of 3 or 5 days. Each group of cell samples contained a negative control (media alone) and a positive control (Concanavalin A, Sigma Chemicals). Cells were pulsed at time of measurement with 0.5 µCurie of tritiated thymidine (ICN Pharmaceuticals) per well. T cells that were specific for hGH proliferated in response to added hGH and incorporated the tritiated thymidine into their DNA. The amount of incorporated tritium was counted 16 to 18 hours post-pulse in a scintillation counter. Data was reported as the stimulation index, which was derived by dividing the counts per minute obtained from the samples divided by the counts per minute obtained from the negative control.

Example 5

This Example compares the immune response elicited using a nucleic acid molecule encoding hGH complexed with either LTI lipid 781-1 or LTI lipid 106-3 to the immune response elicited using a naked DNA vaccine encoding hGH in cats.

The hGH nucleic acid molecule was complexed with LTI lipid 781-1 at a lipid-to-DNA ratio (µg:µg) of 0.5:1.0, and formulated with LTI lipid 106-3 at a lipid-to-DNA ratio of 1:1, as described in Example 2. The naked DNA vaccine consisted of the hGH nucleic acid molecule prepared as described in Example 2 dissolved in saline.

A total of 12 cats were divided into three vaccine groups as follows:

Group 1 (naked DNA): Two injections, spaced 8 weeks apart, of 300 µg of naked hGH nucleic acid molecule in 500 µl saline.

Group 2 (LTI lipid 781-1): Two injections, spaced 8 weeks apart, of 300 µg hGH nucleic acid molecule complexed with 150 µg cationic lipid.

Group 3 (LTI lipid 10-3): Two injections, spaced 8 weeks apart, of 300 µg hGH nucleic acid molecule complexed with 300 µg cationic lipid.

At day 54 post injection, the cats were boosted with another injection of the appropriate cationic lipid-DNA mixture. At day 111, cats were boosted again, and at day 119, T-cell proliferation assays were performed as described. A T-cell stimulation index of 2 is taken as the cutoff and values below 2 are considered non-responsive.

Sera samples were collected from cats following the primary and booster administrations of complex as described in Example 3 and were assayed for hGH specific antibody responses by ELISA. Endpoint ELISA titers are shown in Table 1. The lowest sera titers measured were 1:40. Therefore, negative titers are expressed as <1:40.

TABLE 1 hGH antibody titers of sera samples collected from cats administered a naked DNA vaccine or a complex of the present invention encoding hGH

| cat # | Formulation | Titer at day 54 (post prime) | Titer at day 64 (post boost) | T-cell stimulation index |
| --- | --- | --- | --- | --- |
| 1 | Naked DNA | <1:40 | <1:40 | 9.1 |
| 2 | Naked DNA | <1:40 | <1:40 | 2.4 |
| 3 | Naked DNA | <1:40 | 1:1125 | 12.7 |
| 4 | Naked DNA | <1:40 | <1:40 | 11.3 |
|  |  | geometric mean = 40 | geometric mean = 92 |  |
| 5 | DNA + lipid 781-1 | <1:40 | <1:40 | 1.6 |
| 6 | DNA + lipid 781-1 | 1:160 | 1:10,240 | 20.2 |
| 7 | DNA + lipid 781-1 | 1:2312 | 1:7762 | 3.7 |
| 8 | DNA + lipid 781-1 | 1:233 | 1:21,183 | 8.9 |
|  |  | geometric mean = 242 | geometric mean = 2865 |  |
| 9 | DNA + lipid 106-3 | 1:1076 | 1:19,000 | 24.3 |
| 10 | DNA + lipid 106-3 | 1:316 | 1:19,135 | 65.5 |
| 11 | DNA + lipid 106-3 | <1:40 | <1:40 | 18.2 |
| 12 | DNA + lipid 106-3 | 1:125 | 1:8693 | 2.6 |
|  |  | geometric mean = 203 | geometric mean = 3353 |  |

The results in Table 1 indicate that there was no seroconversion in any of the four cats administered a single inoculation of 300 µg of the naked hGH nucleic acid molecule. Moreover, following the booster administration, only one of the four cats in the naked DNA vaccine group developed an hGH-specific antibody response. In contrast to the naked DNA vaccine group, 75% of the cats (i.e., 3 of 4 cats) cats in each of the two lipid groups developed detectable titers following the primary administration of complex, and these responses went up markedly following the booster administration of complex.

T-cell proliferation, measured by the T cell stimulation index, indicates that all treatments, including treatment with DNA alone, appeared to activate cell-mediated immunity. Treatment with a complex of DNA and lipid 106-3 appears to work better for stimulating T cell proliferation in cats than did naked DNA alone or DNA complexed with lipid 781-1.

Example 6

This Example compares immune responses elicited using a nucleic acid molecule encoding rabies glycoprotein G complexed with several cationic lipids of the present invention to the immune response elicited using a naked DNA vaccine encoding rabies glycoprotein G in cats.

This example compared the abilities of the following compositions to elicit an immune response against rabies glycoprotein G (rabies G) in cats: a naked DNA vaccine consisting of the rabies G nucleic acid molecule; and complexes between the rabies G nucleic acid molecule and one of the following cationic lipids: LTI lipid 106-3, LTI lipid 781-1, or LTI lipid 4518-52, each at a variety of DNA:lipid ratios. Also tested was a complex that had been dehydrated by lyophilization and rehydrated prior to administration. Each of the compositions was produced as described in Example 2. All cats received two intramuscular injections as described in Example 3, spaced four weeks apart. The following groups of 4 cats each were tested:

Group 1: Naked DNA, 300 μg rabies G vector

Group 2: 300 μg lipid 781-1+300 μg rabies G vector

Group 3: 150 μg lipid 781-1+300 μg rabies G vector

Group 4: 75 μg lipid 781-1+300 μg rabies G vector

Group 5: 600 μg lipid 106-3+300 μg rabies G vector

Group 6: 300 μg lipid 106-3+300 μg rabies G vector

Group 7: 150 μg lipid 106-3+300 μg rabies G vector

Group 8: 300 μg lipid 4518-52+300 μg rabies G vector

Group 9: 300 μg lipid 106-3+300 μg rabies G vector (lyophilized and rehydrated)

Group 10: 75 μg lipid 106-3+75 μg rabies G vector.

Group 1 served as a control group to demonstrate immunogenicity of the naked DNA vaccine. Groups 2-4 were designed to determine if differences in the lipid-to-DNA ratio were important for lipid 781-1. Similarly, groups 5–7 were designed to determine if differences in the lipid-to-DNA ratio were important for lipid 106-3. Group 8 was included to examine the efficacy of LTI lipid 4518-52. Group 9 was included to determine if lyophilization and rehydration of lipid:DNA complexes would improve cationic lipid vaccine efficacy in cats as previously demonstrated in mice by Gregoriadis, ibid. Finally, group 10 was included to determine is less than 300 μg of DNA could be used without affecting the ability of lipid 106-3 to enhance the ability of cats to elicit an immune response.

Rabies virus-specific neutralizing antibody activity was measured in the sera of all cats before and after the booster administration by RFFIT. Sera dilutions tested ranged from 1:5 to 1:174,693. Negative responses are listed as a titer of <1:5 while responses that are stronger than the final dilution tested are indicated by the ">" sign. Injections were made intramuscularly. It is known to those skilled in the art that an anti-rabies G antibody titer of 1:5 or greater, as measured by RFFIT, is protective. Results from these studies are shown in Table 2.

TABLE 2

Rabies G antibody titers of sera samples collected from cats administered a naked DNA vaccine or a complex of the present invention encoding rabies G.

| cat # | Formulation | Titer Pre-boost | Titer Post-boost |
|---|---|---|---|
| Group 1 | | | |
| QHR5 | Naked DNA (300 μg rabies G) | <1:5 | 1:25 |
| BWM3 | Naked DNA (300 μg rabies G) | <1:5 | <1:5 |
| 3042 | Naked DNA (300 μg rabies G) | <1:5 | 1:1400 |
| ABO2 | Naked DNA (300 μg rabies G) | <1:5 | <1:5 |
| Group 2 | | | |
| QHH1 | 300 μg DNA + 300 μg lipid 781-1 | 1:7000 | 1:167,449 |
| 3102 | 300 μg DNA + 300 μg lipid 781-1 | 1:1800 | 1:167,449 |
| S72 | 300 μg DNA + 300 μg lipid 781-1 | <1:5 | 1:50 |
| QJB1 | 300 μg DNA + 300 μg lipid 781-1 | <1:5 | 1:230 |
| Group 3 | | | |
| QHN4 | 300 μg DNA + 150 μg lipid 781-1 | <1:5 | 1:1400 |
| QIN5 | 300 μg DNA + 150 μg lipid 781-1 | 1:2200 | 1:42,724 |
| QGN5 | 300 μg DNA + 150 μg lipid 781-1 | 1:625 | 1:113,264 |
| QHG1 | 300 μg DNA + 150 μg lipid 781-1 | <1:5 | 1:7000 |
| Group 4 | | | |
| QHR1 | 300 μg DNA + 75 μg lipid 781-1 | <1:5 | 1:50 |
| QIN2 | 300 μg DNA + 75 μg lipid 781-1 | 1:280 | 1:5100 |
| QGR5 | 300 μg DNA + 75 μg lipid 781-1 | 1:2400 | 1:6000 |
| ACN1 | 300 μg DNA + 75 μg lipid 781-1 | <1:5 | 1:125 |
| Group 5 | | | |
| 3603 | 300 μg DNA + 600 μg lipid 106-3 | 1:7000 | 1:174,693 |
| BNJ2 | 300 μg DNA + 600 μg lipid 106-3 | <1:5 | 1:1800 |
| ZAH1 | 300 μg DNA + 600 μg lipid 106-3 | 1:5100 | 1:159,751 |
| S203 | 300 μg DNA + 600 μg lipid 106-3 | 1:6300 | 1:67A91 |
| Group 6 | | | |
| 3525 | 300 μg DNA + 300 μg lipid 106-3 | 1:280 | 1:45,668 |
| BNJ1 | 300 μg DNA + 300 μg lipid 106-3 | 1:125 | 1:6800 |
| BMX2 | 300 μg DNA + 300 μg lipid 106-3 | <1:5 | 1 :6800 |
| S197 | 300 μg DNA + 300 μg lipid 106-3 | >1:167,449 | 1:6800 |
| Group 7 | | | |
| 3553 | 300 μg DNA + 150 μg lipid 106-3 | 1:1100 | 1:53,888 |
| BN13 | 300 μg DNA + 150 μg lipid 106-3 | <1:5 | 1:3125 |
| E490 | 300 μg DNA + 150 μg lipid 106-3 | 1:25 | 1:6800 |
| S192 | 300 μg DNA + 150 μg lipid 106-3 | 1:40 | 1:6000 |
| Group 8 | | | |
| 3541 | 300 μg DNA + 300 μg lipid 4518-52 | 1:45 | 1:7000 |
| BNH4 | 300 μg DNA + 300 μg lipid 4518-52 | 1:1200 | 1:142,858 |
| BLR1 | 300 μg DNA + 300 μg lipid 4518-52 | 1:280 | 1:7000 |
| S189 | 300 μg DNA + 300 μg lipid 4518-52 | >1:7000 | 1:159,751 |
| Group 9 | | | |
| | DNA + lipid 106-3, dehyd &. rehyd[1] | 1:2700 | 1:142,858 |
| BNF4 | DNA + lipid 106-3, dehyd &. rehyd[1] | 1:170 | >1:167,449 |
| E457 | DNA + lipid 106-3, dehyd &. rehyd[1] | 1:1400 | 1:8,125 |
| S186 | DNA + lipid 106-3, dehyd &. rehyd[1] | 1:45 | 1:3,125 |
| Group 10 | | | |
| BMC1 | DNA, 75 μg + lipid 106-3, 75 μg | 1:1800 | 1:6000 |
| E451 | DNA, 75 μg + lipid 106-3, 75 μg | 1:3125 | 1:38,206 |
| QNV1 | DNA, 75 μg + lipid 106-3, 75 μg | 1:360 | 1:34,600 |
| ZAF1 | DNA, 75 μg + lipid 106-3, 75 μg | 1:440 | 1:5,400 |

[1]300 μg rabies G DNA + 300 μg lipid 106-3/dehydrated and rehydrated by the method of Gregonadis, et al., ibid.

Geometric Mean Titers for each group, pre-boost and post-boost, for each group

| Group | Formulation | mean titer, pre- | mean titer, post- |
|---|---|---|---|
| 1 | Naked DNA (300 µg) | <5 | 30.6 |
| 2 | DNA, 300 µg + lipid 781-1, 300 µg (1:1) | 133 | 4238 |
| 3 | DNA, 300 µg + lipid 781-1, 150 µg (1:0.5) | 77 | 14,756 |
| 4 | DNA, 300 µg + lipid 781-1, 75 µg (1:0.25) | 64 | 661 |
| 5 | DNA, 300 µg + lipid 106-3, 600 µg (1:2) | 1029 | 42,910 |
| 6 | DNA, 300 µg + lipid 106-3, 300 µg (1:1) | 413 | 10,409 |
| 7 | DNA, 300 µg + lipid 106-3, 150 µg (1:0.5) | 48 | 9104 |
| 8 | DNA, 300 µg + lipid 4518-52, 300 µg (1:1) | 570 | 32,518 |
| 9 | DNA, 300 µg + lipid, 1063, 300 µg dehyd& rehyd[1] | 412 | 49,159 |
| 10 | DNA, 75 µg + lipid 106-3, 75 µg (1:1) | 972 | 14,385 |

The data presented in Table 2 support the following conclusions: (1) in the cats receiving the naked DNA vaccine, no seroconversion was observed following the primary administration of vaccine immunization. In contrast, all of the cats receiving a nucleic acid molecule-cationic lipid complex of the present invention exhibited seroconversion after the booster administration, and at least 50% of the cats seroconverted per group after the initial administration of the complex. The best seroconversion was seen in groups 8, 9, and 10 in which 100% seroconversion was observed following the primary administration of complex. These results (0% seroconversion in group 1 and 100% seroconversion in groups 8–10 following the primary administration) were statistically significant by Fisher's exact test (P<0.05). (2) Following the booster administration, all nine groups that were administered a complex of the present invention exhibited stronger responses than the naked DNA vaccine control group. Despite the small number of cats in each group, statistically significant enhancement by Student's t test was observed in groups 5 and 9 as compared to group 1, i.e. naked DNA vaccine. (3) Varying the ratio of lipid-to-DNA did not have significant impact on the degree of enhancement (groups 2-4 and 5-7). (4) Dehydration and rehydration of the lipid:DNA complexes (lipid 106-3) prior to inoculation resulted in 100% seroconversion following the primary administration and very strong responses in all cats following the boost (group 9). (5) Reducing the DNA dosage to 75 kg from 300 µg did not result in any loss of the enhancement potential since 100% seroconversion was observed after the primary administration of the complex and very strong responses were observed in all cats post-boost (group 10).

Example 7. Measuring luciferase expression in cat muscle.

Muscle and lymph node tissues were dissected and removed from the thigh of a sacrificed cat, see Example 3. The tissues were quick frozen on dry ice, and ground to a powder in liquid nitrogen. Ground frozen tissue was resuspended in 1X cell culture lysate reagent (25 mM Tris-Phosphate, pH 7.8, 2 mM DTT, 2 mM 1,2 diaminocyclohexane-N,N,N',N'-tetraacetic acid, 10% glycerol, I1% Triton X-100). After lysis, the cell debris was removed by centrifugation and supernatant was used in the following assay. An aliquot of the supernatant was mixed with Luciferase Assay Reagent, (Promega, Madison, Wis.). The mixture was placed in a Turner Designs Luminometer TD-20/20, (Promega), and the light emitted was measured for 15 seconds. The standard used to calibrate the assay was the recombinant firefly luciferase QUANTILUM™, (Promega).

Example 8

Comparison of expression of a DNA plasmid, formulated with and without LTI lipid 106-3, in the cat muscle.

In this example, evidence for increased antigen expression in the muscle upon formulation with lipid 106-3 was observed in an experiment in which 300 µg of a plasmid vector encoding luciferase was injected into each semimembranosus muscle (inner thigh) of a cat, one muscle receiving DNA complexed with lipid, and one muscle receiving naked DNA. In the case of DNA formulated with lipid 106-3, 300 µg of DNA was formulated with 300 µg of lipid 106-3. Specifically, the right thigh of the cat was injected with DNA alone; the left thigh was injected with DNA formulated with lipid 106-3. After 48 hours, the cat was sacrificed, the muscles were dissected and luciferase activity was measured as described in Example 7. Table 3 shows the luciferase assay standard curve used for this experiment, and Table 4 shows luminometer measurements for each dissected tissue in the cat.

TABLE 3

Luciferase assay standard curve

| Sample | Luminometer readings |
|---|---|
| Blank | 0.069 |
| Positive control | 332 |
| 2.5 µg standard | 387.9 |
| 250 nanogram (ng) standard | 54.07 |
| 25 ng standard | 9.817 |
| 2.5 ng standard | 1.909 |
| 250 picogram (pg) standard | 0.431 |
| 25 pg standard | 0.189 |

TABLE 4

Luminometer readings for each dissected muscle

| muscle tested | Amount of tissue used in luciferase assay | Luminometer reading |
|---|---|---|
| Right superficial muscle (M. gracilis) | 140 milligram (mg) | 0.044 |
| Right deep muscle (M. semimembranosus) | 140 mg | 0.065 |
| Right Inguinal lymph node | 100 mg | 0.040 |
| Right Popliteal lymph node | 73 mg | 0.052 |
| Left superficial muscle | 140 mg | 0.058 |
| Left Deep muscle | 140 mg | 13.82 |
| Left Inguinal lymph node | could not locate | Not determined |
| Left Popliteal lymph node | 80 mg | 0.078 |

While no significant luciferase activity was observed in the leg injected with naked DNA, approximately 2 µg total of luciferase was produced in the entire deep muscle of the leg injected with the lipid/DNA formulation (assay sensitivity=2 pg), providing evidence for enhanced gene delivery and antigen production via use of cationic lipid formulations of the present invention.

Example 9

Effect of cationic lipid formulated DNA vaccines in mice.

This example demonstrates that formulation of DNA vaccines with cationic lipids does not enhance nucleic acid efficacy in mice, in contrast to the enhancement of nucleic acid efficacy seen in cats treated with cationic lipid/DNA formulations.

Three different nucleic acid molecules, encoding rabies glycoprotein G, were prepared as described in Example 2. The first, pMV 5044, contains the CMV intron A promoter, the rabies glycoprotein G coding sequence, and the rabbit beta globin polyadenylation sequence. The second, pMV 5045, contains the CMV intron A promoter, the rabies glycoprotein G coding sequence, and the bovine growth hormone polyadenylation sequence. The third, pMV 5046, contains the CMV promoter, the rabies glycoprotein G coding sequence, and the bovine growth hormone polyadenylation sequence.

The three nucleic acid molecules encoding rabies glycoprotein G (rabies G) were complexed with LTI lipid 106-3 at a lipid to DNA ratio (μg:μg) of 1:1 as described in Example 2. The corresponding "naked" DNA vaccines were prepared by dissolving the plasmids in saline.

A total of 30 mice were divided into six vaccine groups as follows:

Group 1 (pMV 5044, 50 μg+lipid): One injection, intramuscular. Antibody titers determined at four weeks post injection.

Group 2 (pMV 5044, 100 μg alone): One injection, intramuscular. Antibody titers determined at four weeks post injection.

Group 3 (pMV 5045, 50 μg+lipid): One injection, intramuscular. Antibody titers determined at four weeks post injection.

Group 4 (pMV 5045, 100 μg alone): One injection, intramuscular. Antibody titers determined at four weeks post injection.

Group 5 (pMV 5046, 50 μg+lipid): One injection, intramuscular. Antibody titers determined at four weeks post injection.

Group 6 (pMV 5046, 100 μg alone): One injection, intramuscular. Antibody titers determined at four weeks post injection.

TABLE 5

Anti-rabies G antibody titers of sera samples collected from mice administered a naked DNA vaccine or a complex of the present invention encoding rabies G.

| mouse # | Formulation | Titer |
|---|---|---|
| | Group 1 | |
| 1 | pMV5044, 50 μg + Lipid 106-3 | 1:40 |
| 2 | pMV5044, 50 μg + Lipid 106-3 | 1:40 |
| 3 | pMV5044, 50 μg + Lipid 106-3 | 1:51 |
| 4 | pMV5044, 50 μg + Lipid 106-3 | 1:115 |
| 5 | pMV5044, 50 μg + Lipid 106-3 | 1:135 |
| | Group 2 | |
| 1 | pMV5044, 100 μg alone | 1:43 |
| 2 | pMV5044, 100 μg alone | 1:53 |
| 3 | pMV5044, 100 μg alone | 1:242 |
| 4 | pMV5044, 100 μg alone | 1:1060 |
| 5 | pMV5044, 100 μg alone | 1:3795 |
| | Group 3 | |
| 1 | pMV5045, 50 μg + Lipid 106-3 | 1:40 |
| 2 | pMV5045, 50 μg + Lipid 106-3 | 1:65 |
| 3 | pMV5045, 50 μg + Lipid 106-3 | 1:68 |
| 4 | pMV5045, 50 μg + Lipid 106-3 | 1:73 |
| 5 | pMV5045, 50 μg + Lipid 106-3 | 1:137 |
| | Group 4 | |
| 1 | pMV5045, 100 μg alone | 1:1 |
| 2 | pMV5045, 100 μg alone | 1:46 |
| 3 | pMV5045, 100 μg alone | 1:100 |
| 4 | pMV5045, 100 μg alone | 1:547 |
| 5 | pMV5045, 100 μg alone | 1:640 |
| | Group 5 | |
| 1 | pMV5046, 50 μg + Lipid 106-3 | 1:1 |
| 2 | pMV5046, 50 μg + Lipid 106-3 | 1:1 |
| 3 | pMV5046, 50 μg + Lipid 106-3 | 1:1 |
| 4 | pMV5046, 50 μg + Lipid 106-3 | 1:34 |
| 5 | pMV5046, 50 μg + Lipid 106-3 | 1:54 |
| | Group 6 | |
| 1 | pMV5046, 100 μg alone | 1:1 |
| 2 | pMV5046, 100 μg alone | 1:1 |
| 3 | pMV5046, 100 μg alone | 1:1 |
| 4 | pMV5046, 100 μg alone | 1:1 |
| 5 | pMV5046, 100 μg alone | 1:59 |

Rabies-virus specific neutralizing antibody activity was measured by RFFIT in the sera of all mice four weeks after injection with three different nucleic acid molecules containing Rabies glycoprotein G.

The data presented in Table 5 indicate that cationic lipid formulation of a DNA vaccine does not enhance vaccine efficacy, as measured by humoral (antibody) response, in mice. These data are in contrast to results obtained in cats, where vaccine efficacy is enhanced by formulation with cationic lipids. For the nucleic acid construct pMV5044, formulation with lipid actually appears to slightly reduce DNA vaccine efficacy for mice, with the geometric means (of the five mice per group) declining from 294 with DNA alone to 66 with DNA/lipid complex. Results from the other two constructs in mice also showed no increase in efficacy; the geometric means were as follows: for pMVS045, 69.4 for DNA alone and 70.7 with DNA/lipid complex; and for pMV5046, 2.3 for DNA alone and 4.5 for DNA/lipid complex.

Example 10.

Administration of a DNA plasmid, formulated with and without LTI lipid 106-3, to cats.

This example demonstrates the local immune response at the site of injection of DNA plasmids formulated with or without LTI lipid 106-3. Each of four cats was administered each of the following formulations to each of the following sites on the ventral side: (a) saline (i.e., vehicle alone) to the right arm; (b) 300 μg of lipid 106-3 (lipid alone) to the left arm; (c) 300 ;μg of a naked plasmid vector encoding rabies glycoprotein G (naked rabies G vector) to the upper right foot; (d) 300 μg of a naked plasmid vector encoding luciferase (naked luciferase vector) to the lower right foot; (e) 300 μg of rabies G vector formulated with 300 μg of lipid 106-3 to the upper left foot; and (f) 300 μg of luciferase vector formulated with 300 μg of lipid 106-3 to the lower left foot.

Six days after administration of the various formulations, the cats were euthanized and muscle and popliteal lymph node muscles were collected. Although the injection sites were marked, it was difficult to obtain muscle samples from the injection sites; thus, only four injection sites were identified, namely those for the saline only and naked rabies G vector in one cat and those for lipid only and rabies G vector plus lipid in another cat. Muscle samples were sectioned using a cryostat and the sections were stained using hematoxylin and eosin to analyze the population of cells infiltrating the sites of injection. Muscle samples were also stained with antibodies specific for B-cells (anti-CD79a antibodies) using techniques known to those skilled in the art.

No differences were seen among the various lymph nodes with respect to cell infiltration. In the muscle samples where vehicle alone, lipid alone or naked rabies G vector was injected, the infiltrating population of cells were mostly macrophage-like cells. In contrast, in the muscle sample where the formulation comprising rabies G vector complexed with lipid was infected, the infiltrating cells were predominantly lymphocyte-like cells. Staining results with anti-CD79a antibodies suggested that the majority of lymphocytes present were T cells.

These results, as well as others provided herein, suggest that administration of nucleic acid molecules complexed with cationic lipids to cats leads to enhanced expression of the protein encoded by the nucleic acid molecule and infiltration of lymphocytes to the injection site which apparently does not occur when naked nucleic acid molecules are administered in a similar manner. Without being bound by theory, it is believed that this infiltration of lymphocytes might explain the enhanced immune response seen with nucleic acid molecule-cationic lipid complexes of the present invention.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to protect a felid from rabies infection, said method comprising parenterally administering to said felid a composition comprising a purified nucleic acid molecule encoding rabies glycoprotein G, wherein said purified nucleic acid molecule is complexed with a cationic lipid.

2. The method of claim 1, wherein said cationic lipid comprises a tetramethyltetraalkyl spermine analog lipid.

3. The method of claim 1, wherein said composition further encodes an immunomodulator.

4. The method of claim 1, wherein said felid is selected from the group consisting of domestic cats, wild cats and zoo cats.

5. The method of claim 1, wherein said felid is selected from the group consisting of domestic cats, lions, tigers, leopards, panthers, cougars, bobcats, lynx, jaguars, cheetahs and servals.

6. The method of claim 1, wherein the felid is a domestic cat.

7. The method of claim 1, wherein n single administration of said composition elicits an immune response.

8. The method of claim 1, wherein said composition enhances an immune response compared to administration of a naked DNA vaccine encoding rabies glycoprotein G.

9. The method of claim 1, wherein said step of administering said composition is selected from the group consisting of intramuscular administration, intravenous administration, subentaneous administration, intradermal administration and intraperitoneal administration.

10. The method of claim 1, wherein said step of administering effects about 75% seroconversion in a population of felids administered said purified nucleic acid molecule.

11. The method of claim 1, wherein said step of administering effects about 100% seroconversion in a population of felids administered said purified nucleic acid molecule.

12. The method of claim 1, wherein said purified nucleic acid molecule:lipid ratio is from about 1:10 to about 10:1.

13. The method of claim 1, wherein said purified nucleic acid molecule is administered in a dose about 75 micrograms to about 1,000 micrograms.

14. The method of claim 1, wherein said purified nucleic acid molecule is administered in a dose of not more than about 75 micrograms.

15. The method of claim 1, wherein said composition is dehydrated and subsequently rehydrated prior to administration.

16. The method of claim 1, wherein said composition further comprises an excipient.

* * * * *

UNITED STATES PATENT AND TRADEMARK OFFICE
CERTIFICATE OF CORRECTION

PATENT NO. : 6,770,282 B1
DATED : August 3, 2004
INVENTOR(S) : Joel R. Haynes, Ramani S. Wonderling and Dan T. Stinchcomb It is certified that error appears in the above-identified patent and that said Letters Patent is hereby corrected as shown below:

Column 22,
Line 12, please delete "wherein n single" and replace with -- wherein a single --.

Signed and Sealed this

Thirteenth Day of September, 2005

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 27
<212> TYPE: DNA
<213> ORGANISM: Artificial sequence
<220> FEATURE:
<223> OTHER INFORMATION: Synthetic Primer

<400> SEQUENCE: 1
ttcccaacta taccactatc tcgtcta                                   27

<210> SEQ ID NO 2
<211> LENGTH: 28
<212> TYPE: DNA
<213> ORGANISM: Artificial sequence
<220> FEATURE:
<223> OTHER INFORMATION: Synthetic Primer

<400> SEQUENCE: 2
ctagaagcca cagctgccct ccacagag                                  28
```